United States Patent
McNeel et al.

(10) Patent No.: US 9,078,436 B2
(45) Date of Patent: Jul. 14, 2015

(54) METHOD AND APPARATUS FOR THE ENHANCEMENT OF THE BIOCIDAL EFFICACY OF MONOALKYLDITHIOCARBAMATE SALTS

(71) Applicant: Buckman Laboratories International, Inc., Memphis, TN (US)

(72) Inventors: Thomas E. McNeel, Memphis, TN (US); Richard A. Clark, Memphis, TN (US); William C. Ganus, Memphis, TN (US); Richard D. Lusk, Jr., Lake Cormorant, MS (US); Graciela H. Vunk, Como, MS (US); Luis A. Zugno, Germantown, TN (US)

(73) Assignee: Buckman Laboratories International, Inc., Memphis, TN (US)

( * ) Notice: Subject to any disclaimer, the term of this patent is extended or adjusted under 35 U.S.C. 154(b) by 0 days.

(21) Appl. No.: 14/022,254

(22) Filed: Sep. 10, 2013

(65) Prior Publication Data

US 2014/0088190 A1    Mar. 27, 2014

Related U.S. Application Data

(60) Provisional application No. 61/705,416, filed on Sep. 25, 2012.

(51) Int. Cl.
*A01N 47/14* (2006.01)
*A01N 41/12* (2006.01)
*A01N 47/46* (2006.01)
*C02F 1/50* (2006.01)

(52) U.S. Cl.
CPC .............. *A01N 47/14* (2013.01); *A01N 41/12* (2013.01); *A01N 47/46* (2013.01); *C02F 1/50* (2013.01)

(58) Field of Classification Search
None
See application file for complete search history.

(56) References Cited

U.S. PATENT DOCUMENTS

| | | | |
|---|---|---|---|
| 2,292,758 A | 8/1942 | Hite | |
| 2,929,758 A | 3/1960 | Buckman et al. | |
| 3,577,547 A | 5/1971 | Pelissier et al. | |
| 3,856,851 A | 12/1974 | Buckman et al. | |
| 3,973,034 A | 8/1976 | Buckman et al. | |
| 5,045,213 A * | 9/1991 | Bowers | 210/709 |
| 5,505,819 A | 4/1996 | De Witt et al. | |
| 5,527,826 A | 6/1996 | Oppong et al. | |
| 5,599,461 A * | 2/1997 | Peltier et al. | 210/764 |
| 5,633,278 A | 5/1997 | Oppong et al. | |
| 5,719,172 A | 2/1998 | Oppong et al. | |
| 6,627,087 B1 * | 9/2003 | Samaddar et al. | 210/725 |
| 7,347,941 B2 * | 3/2008 | Sava | 210/606 |
| 8,287,893 B2 * | 10/2012 | Crudden | 424/409 |
| 8,614,170 B2 * | 12/2013 | Ali et al. | 507/90 |
| 8,758,562 B2 * | 6/2014 | Krapsch et al. | 162/141 |
| 8,802,120 B2 * | 8/2014 | Crudden | 424/405 |
| 2007/0251889 A1 * | 11/2007 | Singleton et al. | 210/764 |
| 2012/0282349 A1 * | 11/2012 | Tamagawa et al. | 424/633 |
| 2012/0329871 A1 * | 12/2012 | McKinley et al. | 514/533 |
| 2014/0303045 A1 * | 10/2014 | Campbell et al. | 507/128 |

OTHER PUBLICATIONS

International Search Report and Written Opinion issued in corresponding International Patent Application No. PCT/US2013/058842 dated Dec. 6, 2013 (8 pages).
International Preliminary Report on Patentability issued in corresponding International Patent Application No. PCT/US2013/058842 dated Dec. 4, 2014 (21 pages).
Joris et al., "Decomposition of Monoalkyl Dithiocarbamates," Analytical Chemistry, vol. 42, No. 6, May 1970, pp. 647-651.

* cited by examiner

*Primary Examiner* — Robert A Wax
*Assistant Examiner* — Olga V Tcherkasskaya
(74) *Attorney, Agent, or Firm* — Kilyk & Bowersox, P.L.L.C.

(57) ABSTRACT

The present invention provides a method of treating an aqueous system for biocide control, by adding an acidified solution that includes monoalkyldithiocarbamate salt and alkyl isothiocyanate to an aqueous system. A biocide feed system is also provided that is configured to generate a reproducible level of alkyl isothiocyanate. The method and system provide effective levels of alkyl isothiocyanate for rapid biocidal activity, along with levels of monoalkyldithiocarbamate salt which can decompose to form additional alkyl isothiocyanate and provide longer-term biocidal activity.

22 Claims, 9 Drawing Sheets

METHOD AND APPARATUS FOR THE ENHANCEMENT OF THE BIOCIDAL EFFICACY OF MONOALKYLDITHIOCARBAMATE SALTS

This application claims the benefit under 35 U.S.C. §119(e) of prior U.S. Provisional Patent Application No. 61/705,416, filed Sep. 25, 2012, which is incorporated in its entirety by reference herein.

The present invention relates to biocides for a variety of applications, including for use in papermaking, drilling, agricultural products, and the like.

Methyl isothiocyanate (MITC) has been used as a biocide and is highly toxic to bacteria, fungi, algae, nematodes, seeds, and the like. Because MITC is highly toxic, it can be quite dangerous to work with and to handle. For these reasons, salts of methyldithiocarbamate were made since this product decomposes to form MITC. Other compositions at times were added to the dithiocarbamate salt in order to attempt to enhance biocidal efficacy. These attempts did not always lead to highly successful results. In addition, the use of dithiocarbamate salts proved to be quite inconsistent. One possible reason for the inconsistency is due to the possible creation of variable levels of MITC formed during the decomposition and dependent upon its application.

Furthermore, the inventors of the present application have determined that the biocidal efficacy of monoalkyl dithiocarbamate salts depends upon their ability to convert into alkyl isothiocyanates, such as MITC. While the use of these dithiocarbamate salts to decompose into effective levels of MITC has been somewhat successful in the past, it was realized that this success was partly due to the acid papermaking processes which are carried out at a sufficiently low pH, such as 5-6 pH. This condition led to the easy activation of the dithiocarbamate ion by causing some of it to be converted to MITC. However, in the past few years, most papermaking operations are now carried out at an alkaline pH level; and, due to this change, the formation of MITC is remarkably slower when a dithiocarbamate salt is used. Consequently, the formation of MITC is so slow that its use as a biocide is deemed unsuccessful in many alkaline applications. Since the water used in cooling systems and in many applications is kept at an alkaline level for a variety of reasons, including to retard corrosion, and this condition is true for other applications, such as drilling muds and drilling fluids, which generally are maintained at an alkaline pH level to inhibit corrosion and to improve performance of dispersant polymers and other additives in drilling fluids, the previous approach of using a dithiocarbamate salt to decompose into MITC simply would not be effective to control the microorganism population. Accordingly, there is a need in the industries that require the use of biocides, such as MITC, to solve the above-described problems, especially for operations that involve alkaline conditions.

SUMMARY OF THE PRESENT INVENTION

A feature of the present invention is to provide a method to effectively use MITC or similar biocides in alkaline processing systems.

A further feature of the present invention is to provide a system to dose-out a dithiocarbamate salt in a manner that the biocidal efficacy is achieved for the treatment area, such as an aqueous solution.

An additional feature of the present invention is to provide a procedure and/or equipment that will accelerate the conversion of the monoalkyldithiocarbamate salt ion to the corresponding isothiocyanate.

Additional features and advantages of the present invention will be set forth in part in the description that follows, and in part will be apparent from the description, or may be learned by practice of the present invention. The objectives and other advantages of the present invention will be realized and attained by means of the elements and combinations particularly pointed out in the description and appended claims.

To achieve these and other advantages and in accordance with the purposes of the present invention, as embodied and broadly described herein, the present invention relates to a method of treating an aqueous system, such as an alkaline aqueous system, for biocide control. The method includes utilizing an acidified solution that contains one or more monoalkyldithiocarbamate salts and the corresponding alkyl isothiocyanate(s). This acidified solution can then be brought into contact with the aqueous system, such as the alkaline aqueous system, by any technique. The total amount of monoalkyldithiocarbamate (as the dithiocarbamate salt plus the corresponding alkyl isothiocyanate) is preferably present in the aqueous system in an amount of from 1 ppm to 200 ppm, based on weight of the aqueous system. When the aqueous system is alkaline, the alkaline aqueous system remains alkaline upon dispersal of the acidified solution; and microbial control can be achieved.

In the present invention, the method for treating the aqueous system, such as an alkaline aqueous system, can include forming the acidified solution by adding at least one acid, such as an organic acid, to a solution including at least one monoalkyldithiocarbamate salt.

The present invention also provides a biocide feed system configured to generate a reproducible level of an alkyl isothiocyanate, such as methyl isothiocyanate (MITC), in a dilution of a monoalkyldithiocarbamate salt. The system provides effective levels of an alkyl isothiocyanate, such as methyl isothiocyanate (MITC) for rapid biocidal activity, along with levels of a monoalkyldithiocarbamate salt which can decompose gradually to form additional alkyl isothiocyanate and provide longer-term biocidal activity. Methods of generating effective levels of alkyl isothiocyanate are also provided as are methods to control microorganisms.

The delivery system can include a source of monoalkyldithiocarbamate salt, a delivery system to feed the monoalkyldithiocarbamate salt from the source into a liquid stream, a monitoring system to monitor the pH of the liquid stream, and an acid delivery system to feed an acid (or a mixture of acids) into the liquid stream based on a pH detected. A control unit can be provided to control the acid delivery system and to deliver acid into the liquid stream based on a pH detected. The acid delivery system can be in fluid communication with a source of acid. The control unit is configured to deliver acid into the liquid stream so as to maintain a pH of the liquid at from about 2 to about 4, for example, within a range of from about 2.8 to about 3.2, or at a pH of about 3. The control of the acid delivery system may be manual or automated.

A monitoring system can be provided to monitor a concentration of monoalkyldithiocarbamate salt in the liquid stream. The monitoring system can include a source of $Ni^{++}$ ions in fluid communication with the liquid stream, and an absorption detector configured to detect UV absorption of a nickel salt at 365 nm, wherein the nickel salt results from a reaction between the monoalkyldithiocarbamate salt and the $Ni^{++}$ ions. The system can optionally include a monitoring system to monitor a concentration of an alkyl isothiocyanate in the liquid stream, wherein the alkyl isothiocyanate is formed by decomposing of monoalkyldithiocarbamate salt in the liquid stream. The monitoring system can comprise an absorption detector configured to detect UV absorption at 230 nm to detect the alkylisothiocyanate. The system can include a high performance liquid chromatography (HPLC) monitoring system configured to detect alkyl isothiocyanate and Ni-dithiocarbamate in the liquid stream.

It is to be understood that both the foregoing general description and the following detailed description are exemplary and explanatory only and are intended to provide a further explanation of the present invention, as claimed.

The accompanying drawings, which are incorporated in and constitute a part of this application, illustrate some of the features of the present invention and together with the description, serve to explain the principles of the present invention.

BRIEF DESCRIPTION OF THE DRAWINGS

A better understanding of the features and advantages of the present invention can be achieved by reference to the accompanying drawings, which are intended to illustrate, not limit, the present invention.

DETAILED DESCRIPTION OF THE PRESENT INVENTION

According to the present invention, a method of treating an aqueous system, such as an alkaline aqueous system, for biocide control is provided. The method includes contacting an acidified solution of a monoalkyldithiocarbamate salt and alkyl isothiocyanate, with the aqueous system, such as the alkaline aqueous system. The total amount of monoalkyldithiocarbamate (as the dithiocarbamate salt plus the corresponding alkyl isothiocyanate) can be present in the aqueous system in an amount of at least 1 ppm, such as from 1 ppm to 200 ppm, based on weight of the aqueous system, for example, from 5 ppm to 100 ppm, from 10 ppm to 75 ppm, or from 10 ppm to 50 ppm or other amounts. When treating an alkaline aqueous system, the alkaline aqueous system can remain alkaline upon dispersal of the acidified solution in the system. The aqueous system can be a drilling fluid, a papermaking stream, process water stream, process water that contains pulp, a packer fluid, a completion fluid, fracking fluid, and the like. The alkaline aqueous system can have a pH of from 7.1 to 12, for example, from 8 to 10, or other alkaline pH ranges.

For purposes of the present invention, the contacting of the acidified solution with the aqueous system can occur in any number of ways. For instance, the acidified solution can be injected into the aqueous system, the acidified solution can be pumped into the aqueous system, a side stream can be used, or any other means for purposes of introducing the acidified solution into the aqueous system. The term "contacting" can further mean that the acidified solution is being dispersed into the aqueous system or mixed into the aqueous system.

The method can further involve forming the acidified solution by adding at least one acid to a solution comprising at least one monoalkyldithiocarbamate salt. The acid can be one or more organic acids. For example, the acid(s) can be formic acid, benzoic acid, citric acid, or a combination thereof. The acidified solution can have the monoalkyldithiocarbamate salt present in a concentration of from 0.2 wt % to 5 wt %, for example, from 0.5 wt % to 3 wt %, or from 0.5 wt % to 1 wt %, based on the weight of the acidified solution. The acidified solution can have a pH of from 2 to 5, for example, from 3 to 4, or about 3. The acid can have any molar concentration, such as 0.01 M to 2 M. The amount of acid used is an amount to achieve a pH from about 2 to about 5.

The alkyl isothiocyanate can be, comprise, consists essentially of, or consist of methyl isothiocyanate (MITC). Other examples of alkyl isothiocyanates that can be used include, but are not limited to, ethyl isothiocyanate, propyl isothiocyanate, butyl isothiocyanate, and hexyl isothiocyanate.

The monoalkyldithiocarbamate salt can be, comprise, consists essentially of, or consist of potassium N-methyldithiocarbamate. Other examples of monoalkyldithiocarbamate salts include, but are not limited to, sodium N-methyldithiocarbamate, trimethylammonium methyldithiocarbamate, potassium monoethyldithiocarbamate, sodium monoethyldithiocarbamate, trimethylammonium mono ethyldithiocarbamate, potassium monopropyldithiocarbamate, sodium monopropyldithiocarbamate, trimethylammonium monopropyldithiocarbamate, potassium monobutyldithiocarbamate, sodium monobutyldithiocarbamate, trimethylammonium monobutyldithiocarbamate, potassium monohexyldithiocarbamate, sodium monohexyldithiocarbamate, and trimethylammonium monohexyldithiocarbamate.

The alkyl isothiocyanate (such as MITC) can be present in the acidified solution in an amount of up to about 5 wt % based on the total weight of the acidified solution, for example, in an amount of from about 0.01 wt % up to about 3 wt %, from about 0.1 wt % up to about 2 wt %, or up to about 1 wt %. This is the amount or concentration prior to being mixed or otherwise introduced into the aqueous system.

Additional aspects of the present invention are described below. It is to be understood that the specific examples of the terms used below are provided above. For instance, the term "monoalkyldithiocarbamate salt" can be, as indicated above, potassium N-methyldithiocarbamate. Examples of the acid, of the alkyl isothiocyanate, and other components are also provided above to avoid repetition.

The present invention also relates to methods of enhancing the biocidal efficacy of a monoalkyldithiocarbamate salt in a liquid stream and can include delivering monoalkyldithiocarbamate salt into the liquid stream, optionally monitoring the concentration of monoalkyldithiocarbamate salt in the liquid stream, optionally monitoring the pH of the liquid stream, and delivering at least one acid into the liquid stream to generate and maintain a desired pH level. The liquid stream can then be introduced, injected, mixed into, or otherwise brought into contact with a source to be treated, such as an aqueous source, as described above. The acid can be delivered in an amount based on a pH detected by pH monitoring. The amount of acid delivered can be effective to reach or maintain the pH of the liquid stream at a pH of from about 2 to about 4, for example, at a pH of from about 2.8 to about 3.2, or at a pH of about 3. The monoalkyldithiocarbamate salt can be monitored by supplying a source of $Ni^{++}$ ions into the liquid stream or into a sample thereof, reacting the nickel ions with the monoalkyldithiocarbamate salt in the stream or sample, forming a nickel salt, and detecting UV absorption of the nickel salt at 365 nm. The method can also include monitoring a concentration of alkyl isothiocyanate in the liquid stream, wherein the alkyl isothiocyanate is formed by a reaction (or decomposition) of the monoalkyldithiocarbamate salt in the liquid stream. The concentration of alkyl isothiocyanate can be monitored, for example, by detecting UV absorption of alkyl isothiocyanate in the liquid stream at 230 nm or other wavelength depending on the alkyl isothiocyanate. These measurements may be conveniently carried out using HPLC equipment.

According to the present invention, it has been found advantageous to dilute the monoalkyldithiocarbamate salt before it is delivered into the source to be treated, for example, by dilution with water. By controlling the concentration of monoalkyldithiocarbamate salt and the pH (e.g., pH 2-4) of the liquid stream, biocidal efficacy can be optimized. The acid used to maintain the low pH can be one or more acids, such as an organic acid, (e.g., formic acid, benzoic acid, citric acid, or any combination thereof). The formic acid can be used, alone or in combination with one or more other acids.

A biocide feed system can be configured to generate a reproducible level of alkyl isothiocyanate in a liquid stream that includes monoalkyldithiocarbamate salt. The feed system can provide effective levels of alkyl isothiocyanate for rapid biocidal activity, along with levels of monoalkyldithiocarbamate salt which can slowly decompose to gradually form additional monoalkyldithiocarbamate salt, providing longer-term biocidal activity. The feed system can include a source of monoalkyldithiocarbamate salt, a delivery system to feed monoalkyldithiocarbamate salt from the source into a liquid stream, a monitoring system to monitor the pH of the liquid stream, and an acid delivery system to feed an acid into the liquid stream based on a pH detected. A control unit can be provided to control the acid delivery system and to deliver acid into the liquid stream based on a pH detected. The acid delivery system can be in fluid communication with a source of the acid. The control unit can be configured to deliver acid into the liquid stream in amounts that maintain a pH of the liquid stream at a level of from about 2 to about 4, for example, within the range of from about 2.5 to about 3.5, within the range of from about 2.8 to about 3.2, or at a pH of about 3. The control of the acid delivery system may be manual or automated.

The biocide delivery system can be in fluid communication with an aqueous source to be treated, for example, in fluid communication with an industrial stream, such as a process water stream.

The delivery of monoalkyldithiocarbamate salt and acid can be based on levels monitored by the feed system. A monitoring system can be provided to monitor the concentration of monoalkyldithiocarbamate salt in the liquid stream and can include, for example, a UV absorption detector. A source of $Ni^{++}$ ions in fluid communication with the liquid stream can be used to react with PNMDC and an absorption detector can be used that is configured to detect UV absorption of the resulting nickel salt at a wavelength of 365 nm. The nickel salt can result from a reaction between the PNMDC and the $Ni^{++}$ ions.

The delivery of monoalkyldithiocarbamate salt and acid can be controlled based on a monitored level of alkyl isothiocyanate. The feed system can include a monitoring system to monitor a concentration of alkyl isothiocyanate in the liquid stream. The monitoring system can comprise an absorption detector configured to detect UV absorption at a wavelength of 230 nm. The system can further include a high performance liquid chromatography (HPLC) monitoring system configured to detect alkyl isothiocyanate and Ni-dithiocarbamate together in the liquid stream, in real time.

Figure 1:
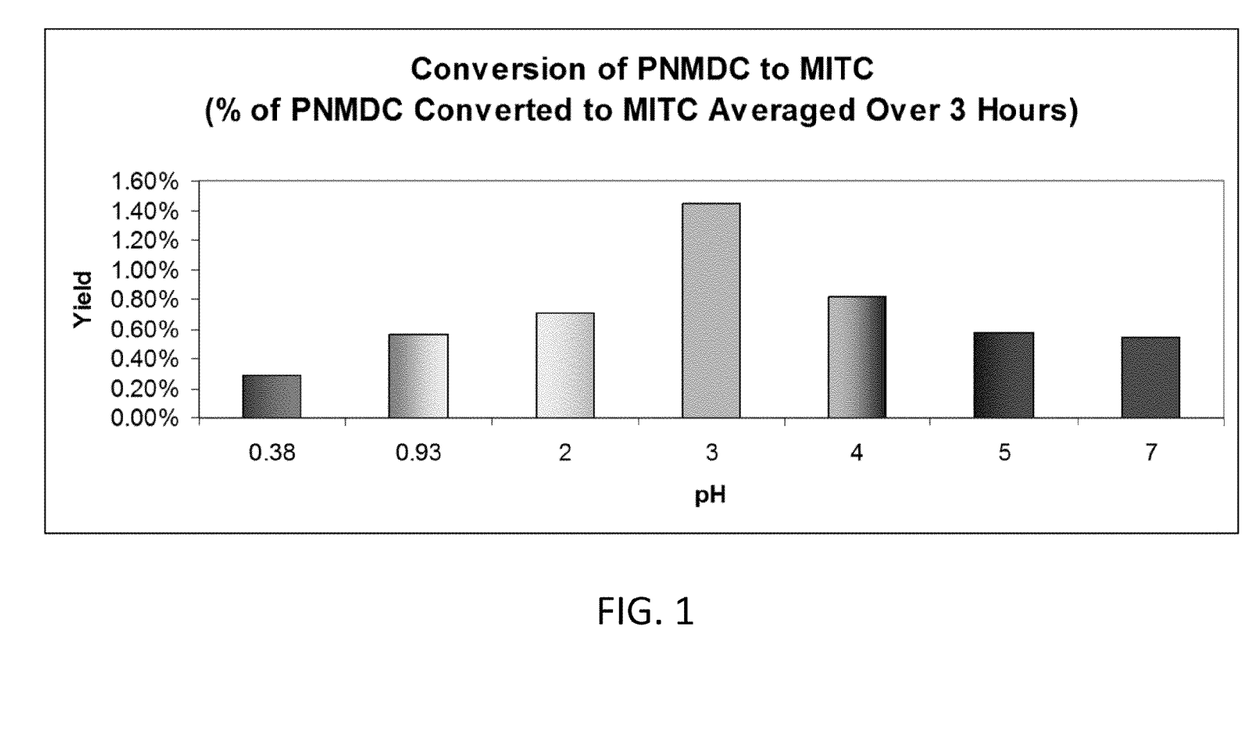
FIG. 1 is a bar graph showing the yield of conversion of potassium N-methyldithiocarbamate (PNMDC) to methyl isothiocyanate (MITC) at various pH levels, over three hours.
Figure 2:
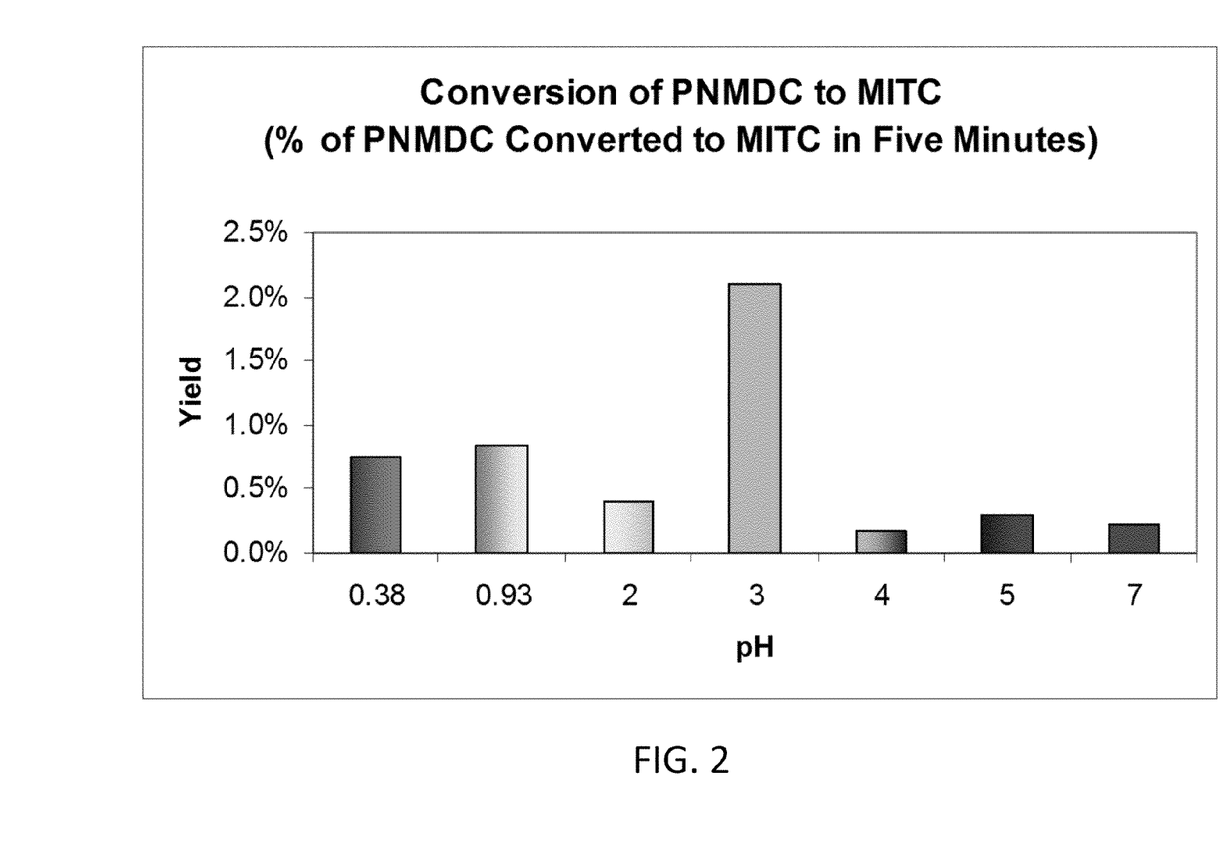
FIG. 2 is a bar graph showing the yield of conversion of potassium N-methyldithiocarbamate (PNMDC) to methyl isothiocyanate (MITC) at various pH levels, over five minutes.

In the decomposition of monoalkyldithiocarbamate salt, the rate at which alkyl isothiocyanate is formed can be determined by the pH of the solution. As just one example, as shown in FIGS. 1 and 2, the yield of conversion from PNMDC to MITC can be dependent upon pH, with the optimum conversion being at pH 3 or about 3. At lower pH levels, a competing reaction, particularly hydrolysis to form carbon disulfide and methylammonium ion, can occur, thus lowering the yield of MITC.

Figure 3:
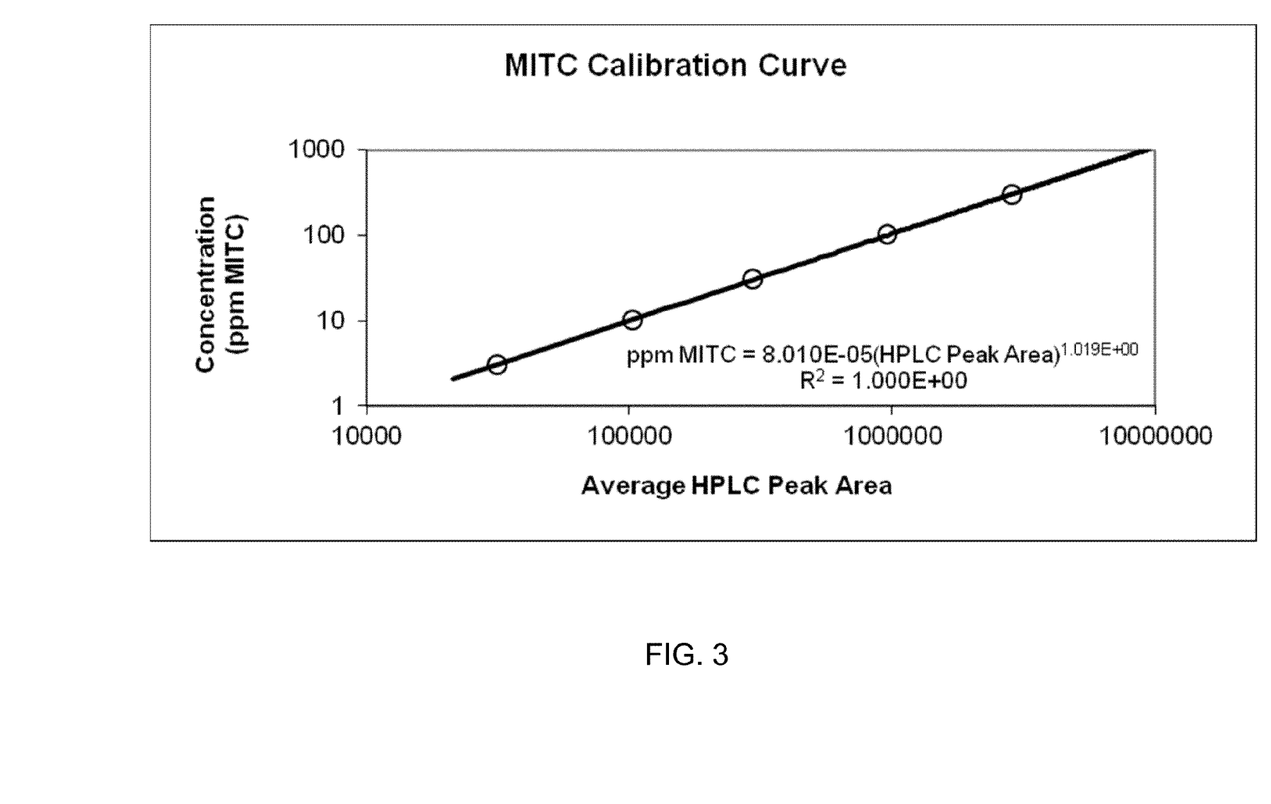
FIG. 3 is a graph showing an MITC calibration curve useful for the detection of MITC by HPLC using a UV/VIS detector set at 230 nm.

Alkyl isothiocyanate, such as methyl isothiocyanate, exhibits end absorption in the short-wave UV spectrum, and it can be detected with reasonably good sensitivity by HPLC using a UV/VIS detector set at 230 nm. FIG. 3 is a graph showing an MITC calibration curve useful for the detection of MITC by HPLC using a UV/VIS detector set at 230 nm. The method shows good linearity over the range of 3-1000 ppm. Due to its high vapor pressure, methyl isothiocyanate (MITC) can be readily detected using gas chromatography or, preferably, GC/MS. Monomethyldithiocarbamate ion can also be detected at very low levels by adjusting the pH of the solution to 7, followed by purge-and-trap/GC or GC/MS analysis.

Dithiocarbamate ion, in both monomethyl and dimethyl forms, can form water-insoluble green-colored compounds when reacted with $Ni^{++}$ and the compounds can be readily detectable, for example, using colorimetric analysis. These compounds are soluble in organic solvents like acetonitrile. An exemplary compound resulting from a reaction with $Ni^{++}$ can be:

A number of other organic functional groups can be substituted for the methyl groups in this compound.

The nickel complexes mentioned above are readily detected by reverse-phase HPLC using a UV/VIS detector.

This HPLC technique can be used to detect dithiocarbamate ion in neat products or in dilute solutions, for example, aqueous solutions having ion concentrations of 1000 ppm or less.

Figure 4:
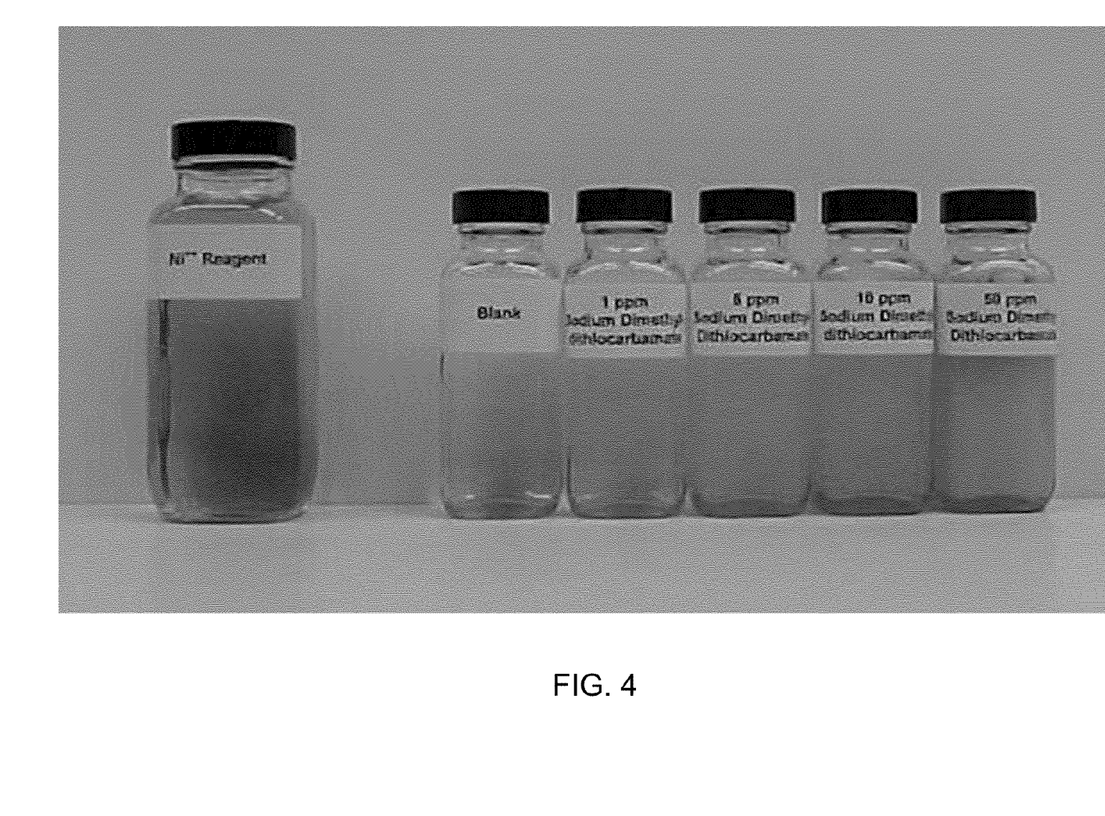
FIG. 4 is a photograph showing a turbidimetric method of determining a concentration of dimethyldithiocarbamate ion by using a precipitation with $Ni^{++}$ ions.

The formation of this precipitate with $Ni^{++}$ can be used to develop a turbidimetric method for detecting and measuring monoalkyldithiocarbamate salt ion. A 5% solution of nickel acetate in 5 M acetate buffer (e.g., pH 5) is added to the sample, and the resulting turbidity is directly related to the concentration of dimethyldithiocarbamate ion. FIG. 4, although in black-and-white, shows that when using a $Ni^{++}$ reagent, solutions of sodium dimethyl dithiocarbamate salt are progressively darker as the concentration of the salt increases from 1 ppm to 50 ppm. In color, the solution turns from lighter green to darker green as the concentration of the salt increases. The $Ni^{++}$ reagent can thus be useful in a turbidimetric method for detecting different levels of the salt.

Figure 5:
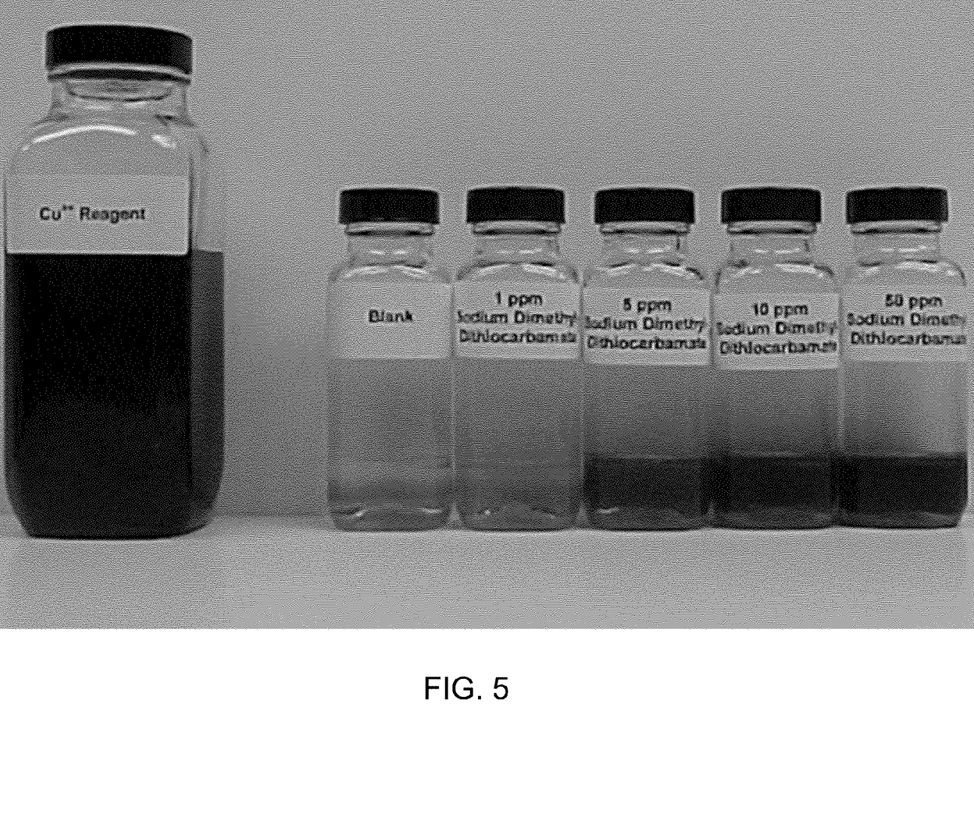
FIG. 5 is a photograph showing a very sensitive colorimetric method of determining a concentration of dithiocarbamate salts by using a Cu++ reagent, for example, $Cu(NH_3)_x^{++}$.
Figure 6:
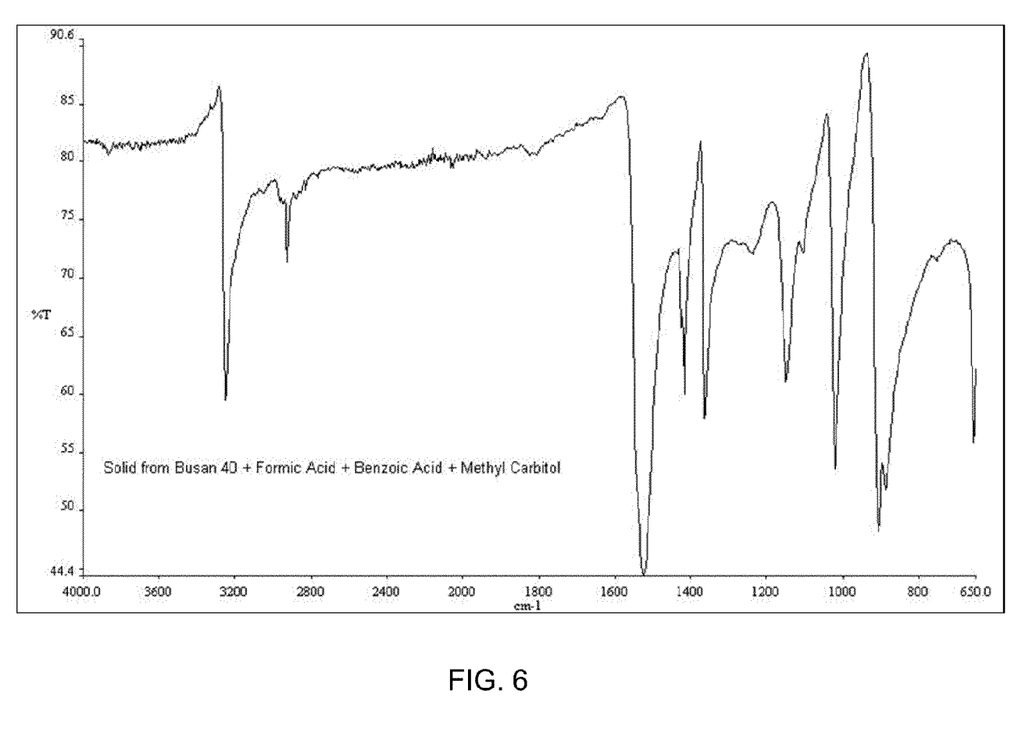
FIG. 6 is a Fourier transform infrared spectrum of the dimer shown in FIG. 7.

Ellman's Reagent (5,5-dithiobis(2-nitrobenzoic acid) or DTNB) can be used in a colorimetric method for the determination of dithiocarbamate salts and different concentrations thereof. Compounds containing —SH or —S⁻ functional groups will reduce the —S—S— bond in DTNB to produce a yellow thiol compound, shown below, which has a strong absorbance at 412 nm:

Dithiocarbamate ion, in either the monomethyl or dimethyl form, will form water-insoluble compounds with $Cu^{++}$, and these compounds are soluble in certain organic solvents. A very sensitive colorimetric method is based on the reaction of the dithiocarbamate ion with an alkaline solution of $Cu(NH_3)_x^{++}$. FIG. 5, although in black-and-white, shows that when using a $Cu^{++}$ reagent, solutions of sodium dimethyl dithiocarbamate salt are progressively darker as the concentration of the salt increases from 1 ppm to 50 ppm. The $Cu^{++}$ reagent can thus be useful in a colorimetric method for detecting different levels of the salt. Similar results may be obtained using a monomethyldithiocarbamate salt instead of the dimethyldithiocarbamate salt.

In classical analytical procedures, dithiocarbamates can be analyzed by conversion to carbon disulfide, which is distilled out of a strongly-acidic sample solution and trapped in alcoholic NaOH to form sodium ethyl xanthate. The sodium ethyl xanthate can subsequently be detected and measured by iodometric titration:

Trace levels of dithiocarbamate ion can be detected by trapping the carbon disulfide in Vile's Reagent (a solution of cupric acetate and diethylamine in water/ethanol):

The copper dithiocarbamate complex is soluble in the aqueous ethanol solvent, and the concentration can be determined by measuring the absorbance at 380 nm.

One other approach to the determination of trace levels of dithiocarbamates can involve the neutralization of the sample solution (buffered at pH 7) and analyzed by purge-and-trap GC/MS. In this technique, the monomethyldithiocarbamate ion will hydrolyze to form MITC, which is swept out of the solution by the purge gas and is trapped as the decomposition reaction proceeds. Likewise, carbon disulfide, which is produced by the hydrolysis of dimethyldithiocarbamate ion, is swept out of the solution by the purge gas and is trapped as the reaction proceeds. The trap is subsequently desorbed into the gas chromatograph, and the separated MITC and carbon disulfide are determined by mass spectrometry or by a flame photometric detector (FPD).

The present invention will be further clarified by the following examples, which are intended to be exemplary of the present invention.

EXAMPLES

BUSAN® 40 is a 32.5% solution of potassium N-methyldithiocarbamate (PNMDC). Biocidal performance of the product was tested to develop a technique to generate a reproducible level of MITC in a dilution of BUSAN® 40. A biocide feed system was designed to provide MITC, for a rapid kill, along with PNMDC that will slowly decompose to form additional MITC and provide longer-term biocidal activity.

The rate and extent of conversion of PNMDC to MITC was found to be strongly affected by pH. While good conversion can occur over a range of pH values, the results shown in FIGS. 1 and 2 indicate an optimum conversion occurring at about pH 3 (e.g., 2.5-3.5).

Figure 9:
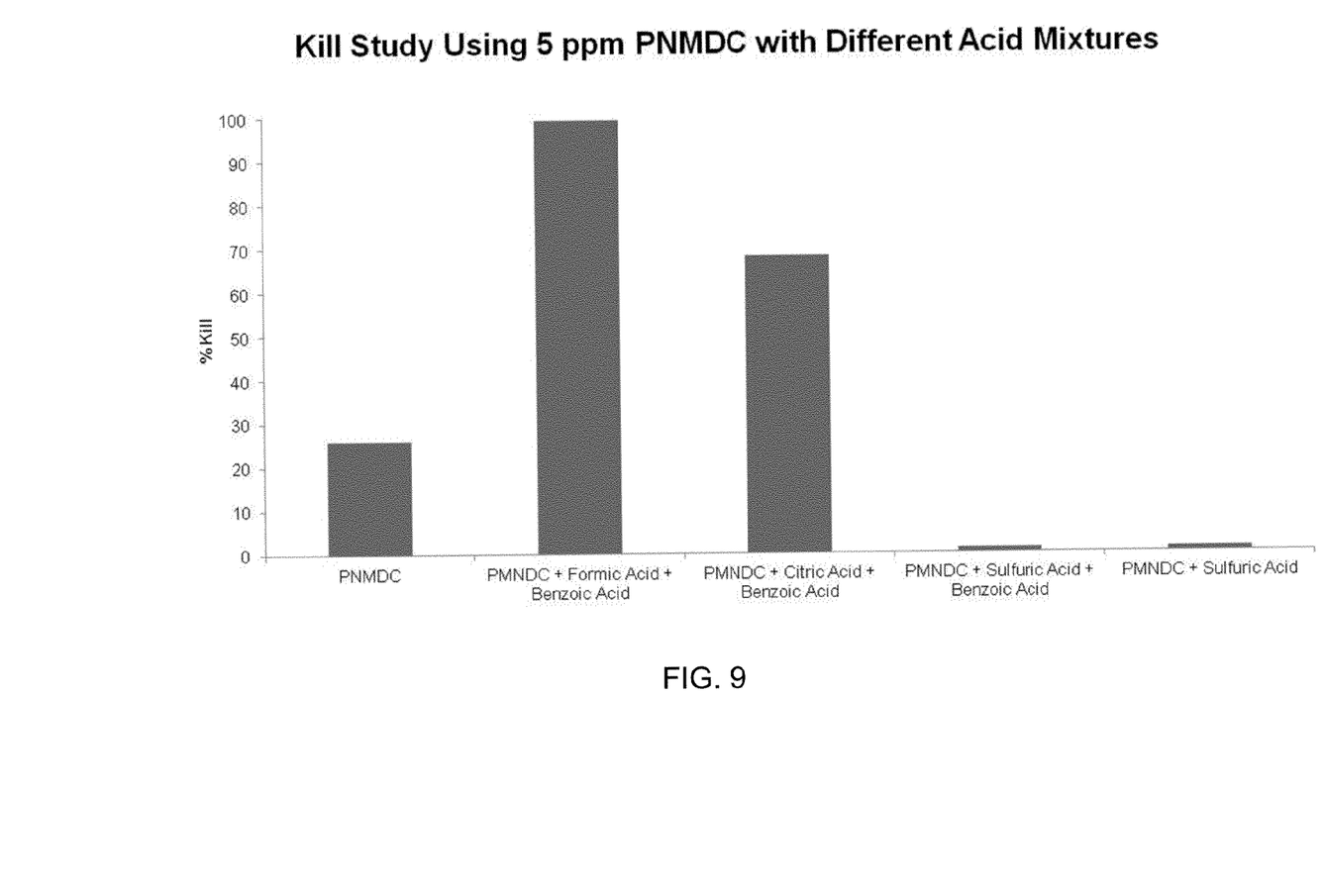
FIG. 9 is a bar graph showing the percent kill for microbiological testing of mixtures of PNMDC with various combinations of acids.

The acids tested were selected from those that are already approved by the EPA as inert ingredients for biocidal products. TABLE 1 below lists the acids tested and their respective properties.

TABLE 1

| Acid | pKa | pH of 0.1M Solution | Solubility in Water |
|---|---|---|---|
| Benzoic Acid | 4.21 | 2.61 | 0.34% |
| Acetic Acid | 4.76 | 2.88 | Miscible |
| Citric Acid (1) | 3.09 | 2.06 | 42% |
| Citric Acid (2) | 4.75 | 2.88 | 42% |
| Formic Acid | 3.77 | 2.39 | Miscible |

A solution of PNMDC was formed by diluting BUSAN® 40 in water to achieve a concentration of approximately 1% PNMDC. The pH was reduced to 3.0±0.2, using one or more of the acids listed in Table 1, and the solution was held at that pH for five minutes before adding additional PNMDC.

An HPLC method was developed to allow the reaction mixtures to be analyzed in real time. This procedure stopped the decomposition of PNMDC by converting any unreacted dithiocarbamate ion to a stable nickel salt:

This compound was then detected by its UV absorption at 365 nm. MITC is unaffected by the presence of the $Ni^{++}$ ion and is detected by its UV absorption at 230 nm.

Figure 7:
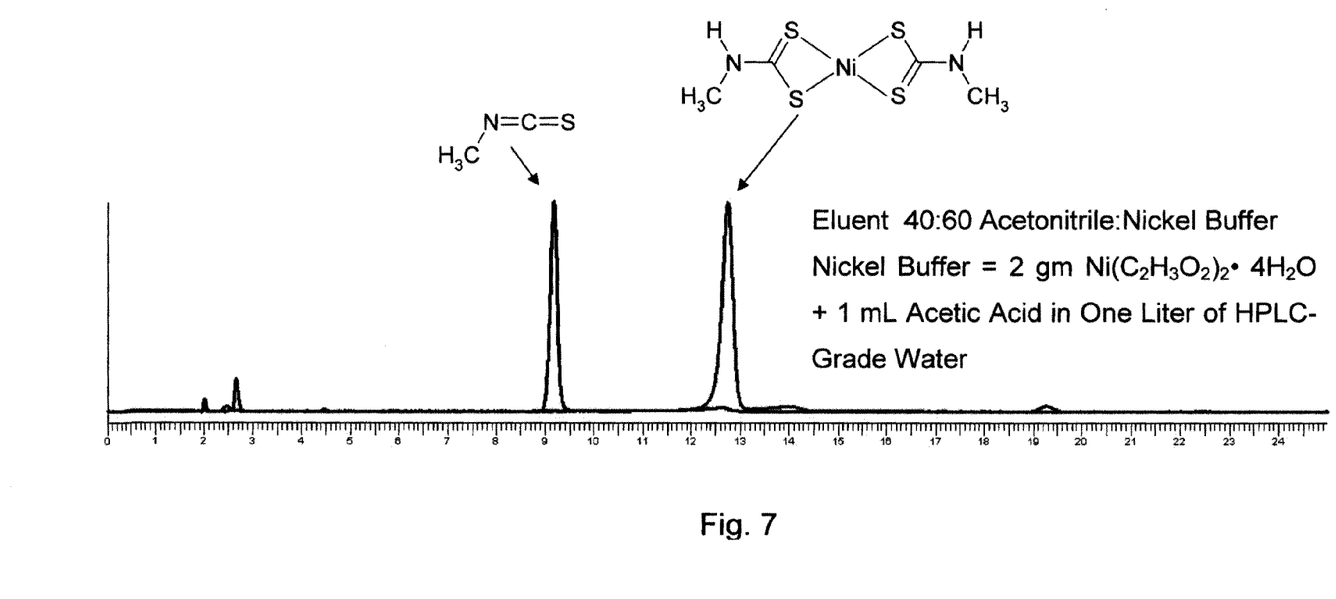
FIG. 7 is an HPLC analysis chromatogram showing a peak for MITC and a peak for a stable nickel salt of PNMDC, having good peak separation in a relatively short chromatogram, enabling analysis of reaction mixtures in real time.

The HPLC analysis provides good separation of the MITC and Ni-PNMDC peaks in a relatively short chromatogram (15 minutes), as shown in FIG. 7.

Equipment was assembled to allow for continuous dilution of BUSAN® 40 with makeup water and to combine an acid mixture with the diluted solution. The liquid handling components of the system were made entirely of perfluoroalkane (PFA) plastic. Peristaltic pumps were used for feeding the BUSAN® 40 and the acid mixture. A schematic diagram of the system is shown in FIG. 8.

Figure 8:
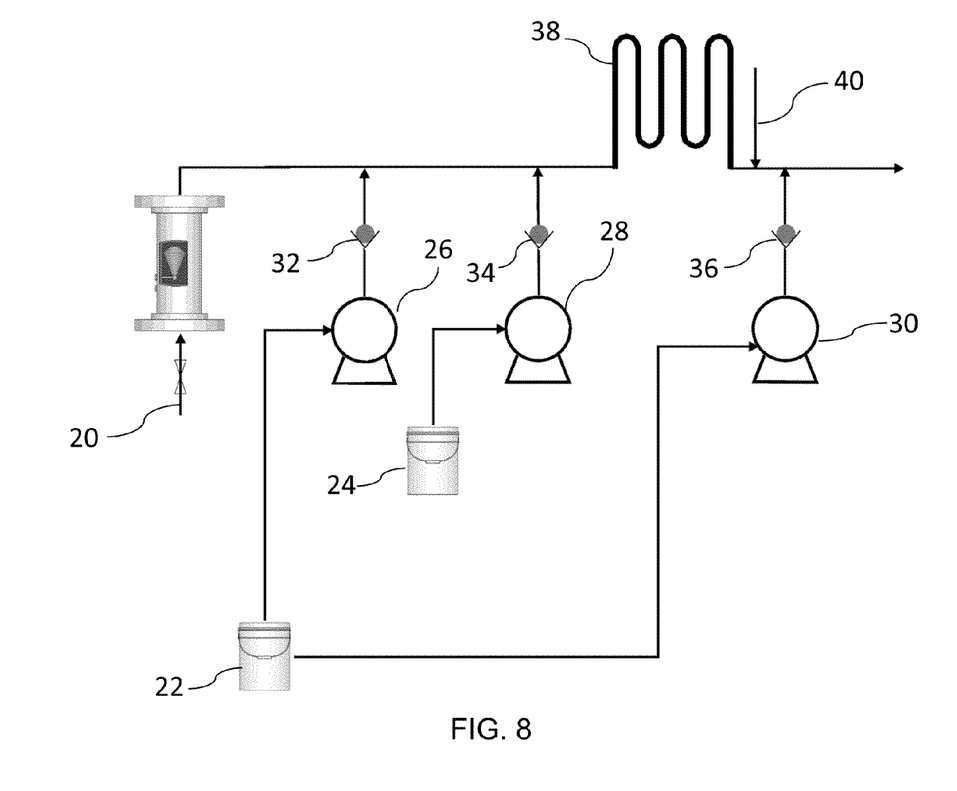
FIG. 8 is a schematic diagram of a dynamic feed system for maintaining biocidal activity in a liquid system and provides for continuous dilution of PNMDC (BUSAN® 40) with makeup water and for combining the diluted product with an acid mixture.

As shown in FIG. 8, the feed system can include a source of a liquid stream (20), such as a source of water, a source of monoalkyldithiocarbamate salt, like PNMDC (22), such as BUSAN 40, a source of an acid (24), such as formic acid, and a series of pumps and check valves. The pumps can include a first pump 26, such as a peristaltic pump for pumping the monoalkyldithiocarbamate salt into water supplied by source 20 to thus form diluted monoalkyldithiocarbamate salt. A second pump 28, such as a peristaltic pump, can be included for pumping the acid or an acid mixture into the diluted monoalkyldithiocarbamate salt. In addition, a third pump 30, such as a peristaltic pump, can be included for optionally pumping additional monoalkyldithiocarbamate salt into the liquid stream at a location downstream of the acid addition. Check valves 32, 34, and 36 can be provided for pumps 26, 28, and 30, respectively, to regulate the pumping of monoalkyldithiocarbamate salt and acid and to prevent backflow of liquid toward the pumps. To facilitate thorough mixing of the acid and diluted monoalkyldithiocarbamate salt, a length of tubing 38 can be provided after the point of acid addition and before the pH of the resulting mixture is measured. Tubing 38 can be, for example, seven meters of ½ inch outer diameter PFA tubing, for example, arranged in a serpentine configuration. This provides a 5-minute residence time before reaching the pH electrode. Downstream of tubing 38, a pH electrode 40 or other pH measuring device can be provided to monitor the pH of the liquid stream and the results obtained from electrode 40 can be used to control the addition of more monoalkyldithiocarbamate salt using pump 26, to control the addition of more monoalkyldithiocarbamate salt using pump 30, and/or to control the addition of more acid or acid mixture using pump 28.

Microbiological testing was conducted using pulp substrate medium, which is described in U.S. Pat. No. 2,881,070 (and incorporated by reference herein). The results are shown below in TABLE 2:

TABLE 2

| Sample # | Sample Description | pH | Dosage (ppm PNMDC) | % Kill |
|---|---|---|---|---|
| 1 | 5000 ppm PNMDC | 10.4 | 5 | 26 |
|   |   |   | 10 | 99.7 |
|   |   |   | 30 | 100 |
| 2 | 5000 ppm PNMDC + 1 wt % Formic Acid + 0.15 wt % Benzoic Acid | 3.3 | 5 | 99.2 |
|   |   |   | 10 | 100 |
|   |   |   | 30 | 100 |
| 3 | 5000 ppm PNMDC + 1 wt % Citric Acid + 0.15 wt % Benzoic Acid | 3.6 | 5 | 68 |
|   |   |   | 10 | 100 |
|   |   |   | 30 | 100 |
| 4 | 5000 ppm PNMDC + 0.17 wt % Sulfuric Acid + 0.15 wt % Benzoic Acid | 3.1 | 5 | 0 |
|   |   |   | 10 | 0 |
|   |   |   | 30 | 100 |
| 5 | 5000 ppm PNMDC + 0.17 wt % Sulfuric Acid (No Benzoic Acid) | 3.1 | 5 | 0 |
|   |   |   | 10 | 0 |
|   |   |   | 30 | 100 |

The results show that the efficacy of BUSAN® 40 (PNMDC) can definitely be enhanced by adding a small amount of certain organic acids shortly before the biocide is fed to a papermaking system. Of the acids considered here, the use of formic acid provided the best biocidal efficacy although the use of benzoic acid, citric acid, and combinations thereof was effective. The acidification step was very useful. Concentrations and residence times can be controlled to prevent undesired side reactions that would lead to precipitation and/or a loss of biocidal efficacy.

These results indicate that biocidal efficacy can be enhanced by acidification shortly before monoalkyldithiocarbamate salt is fed to a papermaking system or other process stream or aqueous source. Adding small amounts of formic acid and benzoic acid can provide further biocidal optimization.

The present invention includes the following aspects/embodiments/features in any order and/or in any combination:

1. The present invention relates to a method of treating an alkaline aqueous system for biocide control, comprising contacting an acidified solution that comprises a monoalkyldithiocarbamate salt and alkyl isothiocyanate, with said alkaline aqueous system, wherein the total amount of monoalkyldithiocarbamate (calculated as the alkylisothiocyanate and the dithiocarbamate salt) is present in said alkaline aqueous system in an amount of from 1 ppm to 200 ppm, based on weight, and wherein said alkaline aqueous system remains alkaline upon dispersal of said acidified solution.
2. The method of any preceding or following embodiment/feature/aspect, wherein said amount is from 5 ppm to 100 ppm.
3. The method of any preceding or following embodiment/feature/aspect, wherein said amount is from 10 ppm to 75 ppm.
4. The method of any preceding or following embodiment/feature/aspect, wherein said amount is from 10 ppm to 50 ppm.
5. The method of any preceding or following embodiment/feature/aspect, wherein said alkaline aqueous system is a drilling fluid.

6. The method of any preceding or following embodiment/feature/aspect, wherein said alkaline aqueous system is a papermaking stream.

7. The method of any preceding or following embodiment/feature/aspect, wherein said alkaline aqueous system is process water that comprises pulp.

8. The method of any preceding or following embodiment/feature/aspect, wherein said alkaline aqueous system is or is used as cooling water.

9. The method of any preceding or following embodiment/feature/aspect, wherein said alkaline aqueous system is a packer fluid, completion fluid, or fracking fluid.

10. The method of any preceding or following embodiment/feature/aspect, wherein said alkaline aqueous system has a pH of from 7.1 to 12.

11. The method of any preceding or following embodiment/feature/aspect, wherein said alkaline aqueous system has a pH of from 8 to 10.

12. The method of any preceding or following embodiment/feature/aspect, wherein said method further comprises forming said acidified solution by adding at least one acid to a solution comprising at least one monoalkyldithiocarbamate salt.

13. The method of any preceding or following embodiment/feature/aspect, wherein said acidified solution comprises formic acid, benzoic acid, citric acid, or a combination thereof.

14. The method of any preceding or following embodiment/feature/aspect, wherein said acidified solution has said monoalkyldithiocarbamate salt present in a concentration of from 0.2 wt % to 5 wt %.

15. The method of any preceding or following embodiment/feature/aspect, wherein said acidified solution has said monoalkyldithiocarbamate salt present in a concentration of from 0.5 wt % to 3 wt %.

16. The method of any preceding or following embodiment/feature/aspect, wherein said acidified solution has said monoalkyldithiocarbamate salt present in a concentration of from 0.5 wt % to 1 wt %.

17. The method of any preceding or following embodiment/feature/aspect, wherein said acidified solution has a pH of from 2 to 5.

18. The method of any preceding or following embodiment/feature/aspect, wherein said acidified solution has a pH of from 3 to 4.

19. The method of any preceding or following embodiment/feature/aspect, wherein said alkyl isothiocyanate comprises methyl isothiocyanate (MITC) present in said acidified solution in an amount of up to about 2 wt % based on the total weight of the acidified solution.

20. The method of any preceding or following embodiment/feature/aspect, wherein the monoalkyldithiocarbamate salt comprises potassium N-methyldithiocarbamate.

21. A biocide feed system comprising:
a source of a monoalkyldithiocarbamate salt;
a biocide delivery system to feed the a monoalkyldithiocarbamate salt from the source into a liquid stream;
a monitoring system to monitor the pH of the liquid stream;
an acid delivery system to feed an acid into the liquid stream; and
a control unit to control the acid delivery system to deliver acid into the liquid stream based on a pH of the liquid stream determined by the monitoring system.

22. The biocide feed system of any preceding or following embodiment/feature/aspect, wherein the acid delivery system is in fluid communication with a source of acid, and the acid comprises formic acid, benzoic acid, citric acid, or a combination thereof.

23. The biocide feed system of any preceding or following embodiment/feature/aspect, wherein the acid delivery system is in fluid communication with a source of formic acid and is configured to deliver formic acid from the source into the liquid stream.

24. The biocide feed system of any preceding or following embodiment/feature/aspect, wherein the control unit is configured to deliver acid into the liquid stream so as to maintain a pH of the liquid stream at from about 2 to about 4. The pH control may be manual or automated.

25. The biocide feed system of any preceding or following embodiment/feature/aspect, wherein control unit is configured to deliver acid into the liquid stream so as to maintain a pH of the liquid stream at about 3.

26. The biocide feed system of any preceding or following embodiment/feature/aspect, further comprising a monoalkyldithiocarbamate salt monitoring system to monitor a concentration of monoalkyldithiocarbamate salt in the liquid stream.

27. The biocide feed system of any preceding or following embodiment/feature/aspect, wherein the monitoring system comprises source of $Ni^{++}$ ions in fluid communication with the liquid stream, and an absorption detector configured to detect UV absorption of a nickel salt at 365 nm.

28. The biocide feed system of any preceding or following embodiment/feature/aspect, further comprising an alkyl isothiocyanate monitoring system to monitor a concentration of alkyl isothiocyanate in the liquid stream.

29. The biocide feed system of any preceding or following embodiment/feature/aspect, wherein the monitoring system comprises an absorption detector configured to detect UV absorption at about 230 nm.

30. The biocide feed system of any preceding or following embodiment/feature/aspect, further comprising a high performance liquid chromatography (HPLC) monitoring system configured to detect the monoalkyldithiocarbamate salt, a byproduct thereof, or both, in the liquid stream.

31. The biocide feed system of any preceding or following embodiment/feature/aspect, further comprising a liquid stream, wherein the biocide delivery system is in fluid communication with the liquid stream.

32. The biocide feed system of any preceding or following embodiment/feature/aspect, wherein the liquid stream comprises a recirculating papermaking pulp or a drilling fluid.

33. A method of enhancing the biocidal efficacy of a monoalkyldithiocarbamate salt in a treatment area, the method comprising:
delivering monoalkyldithiocarbamate salt into a liquid stream;
monitoring the concentration of monoalkyldithiocarbamate salt in the liquid stream;
monitoring the pH of the liquid stream;
delivering at least one acid into the liquid stream, the acid being delivered in an amount based on a pH detected by the monitoring, wherein the amount of acid delivered is effective to maintain the pH of the liquid stream at a pH of from about 2 to about 4;
optionally monitoring a concentration of alkyl isothiocyanate in the liquid stream, the alkyl isothiocyanate being formed by decomposition of the monoalkyldithiocarbamate salt in the liquid stream; and optionally adding additional monoalkyldithiocarbamate salt to the liquid stream based on the monitored concentration of alkyl isothiocyanate in the liquid stream.

34. The method of any preceding or following embodiment/feature/aspect, wherein the monoalkyldithiocarbamate salt is monitored by supplying a source of Ni$^{++}$ ions into the liquid stream, reacting the nickel ions with monoalkyldithiocarbamate salt in the liquid stream to form a nickel salt, and detecting UV absorption of the nickel salt at about 365 nm.

35. The method of any preceding or following embodiment/feature/aspect, wherein the concentration of alkyl isothiocyanate in the liquid stream is monitored by detecting UV absorption of alkyl isothiocyanate in the liquid stream at about 230 nm.

36. The method of any preceding or following embodiment/feature/aspect, further comprising introducing said liquid stream containing monoalkyldithiocarbamate salt and alkyl isothiocyanate into the treatment area.

The present invention can include any combination of these various features or embodiments above and/or below as set forth in sentences and/or paragraphs. Any combination of disclosed features herein is considered part of the present invention and no limitation is intended with respect to combinable features.

The entire contents of all references cited in this disclosure are incorporated herein in their entireties, by reference. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

Other embodiments of the present invention will be apparent to those skilled in the art from consideration of the present specification and practice of the present invention disclosed herein. It is intended that the present specification and examples be considered as exemplary only with a true scope and spirit of the invention being indicated by the following claims and equivalents thereof.

What is claimed is:

1. A method of controlling microorganisms in an alkaline aqueous system comprising
   (i) forming an acidified solution by adding one or more organic acids to a liquid stream comprising a monoalkyldithiocarbamate salt,
      wherein the acidified solution has a pH of from 2 to 5, and
      wherein the acidified solution comprises monoalkyldithiocarbamate salt and alkyl isothiocyanate, and
   (ii) contacting said acidified solution with said alkaline aqueous system to make a total amount of monoalkyldithiocarbamate salt and alkyl isothiocyanate present in said alkaline aqueous system from 1 ppm to 200 ppm, based on weight of the aqueous system, and wherein said alkaline aqueous system remains alkaline upon dispersal of said acidified solution.

2. The method of claim 1, wherein said amount is from 5 ppm to 100 ppm.

3. The method of claim 1, wherein said amount is from 10 ppm to 75 ppm.

4. The method of claim 1, wherein said amount is from 10 ppm to 50 ppm.

5. The method of claim 1, wherein said alkaline aqueous system is a drilling fluid.

6. The method of claim 1, wherein said alkaline aqueous system is a papermaking stream.

7. The method of claim 1, wherein said alkaline aqueous system is process water that comprises pulp.

8. The method of claim 1, wherein said alkaline aqueous system is a packer fluid, completion fluid, or fracking fluid.

9. The method of claim 1, wherein said alkaline aqueous system has a pH of from 7.1 to 12.

10. The method of claim 1, wherein said alkaline aqueous system has a pH of from 8 to 10.

11. The method of claim 1, wherein said acidified solution comprises formic acid, benzoic acid, citric acid, or a combination thereof.

12. The method of claim 1, wherein said acidified solution has said monoalkyldithiocarbamate salt present in a concentration of from 0.2 wt % to 5 wt %.

13. The method of claim 1, wherein said acidified solution has said monoalkyldithiocarbamate salt present in a concentration of from 0.5 wt % to 3 wt %.

14. The method of claim 1, wherein said acidified solution has said monoalkyldithiocarbamate salt present in a concentration of from 0.5 wt % to 1 wt %.

15. The method of claim 1, wherein said acidified solution has a pH of from 2.8 to 3.2.

16. The method of claim 1, wherein said acidified solution has a pH of from 3 to 4.

17. The method of claim 1, wherein said alkyl isothiocyanate comprises methyl isothiocyanate (MITC) present in said acidified solution in an amount of up to about 2 wt % based on the total weight of the acidified solution.

18. The method of claim 1, wherein the monoalkyldithiocarbamate salt comprises potassium N-methyldithiocarbamate.

19. A method for biocide control in a treatment area, the method comprising:
   delivering monoalkyldithiocarbamate salt into a liquid stream;
   monitoring the concentration of monoalkyldithiocarbamate salt in the liquid stream;
   monitoring the pH of the liquid stream;
   delivering at least one acid into the liquid stream, the acid being delivered in an amount based on a pH detected by the monitoring, wherein the amount of acid delivered is effective to maintain the pH of the liquid stream at a pH of from about 2 to about 4, wherein the at least one acid includes formic acid, benzoic acid, citric acid, or a combination thereof;
   optionally monitoring a concentration of alkyl isothiocyanate in the liquid stream, the alkyl isothiocyanate being formed by decomposition of the monoalkyldithiocarbamate salt in the liquid stream;
   optionally adding additional monoalkyldithiocarbamate salt to the liquid stream based on the monitored concentration of alkyl isothiocyanate in the liquid stream; and
   introducing said liquid stream containing monoalkyldithiocarbamate salt and alkyl isothiocyanate into the treatment area.

20. The method of claim 19, wherein the monoalkyldithiocarbamate salt is monitored by supplying a source of Ni$^{++}$ ions into the liquid stream, reacting the nickel ions with monoalkyldithiocarbamate salt in the liquid stream to form a nickel salt, and detecting UV absorption of the nickel salt at about 365 nm.

21. The method of claim 19, wherein the concentration of alkyl isothiocyanate in the liquid stream is monitored by detecting UV absorption of alkyl isothiocyanate in the liquid stream at about 230 nm.

22. The method of claim 1, wherein said alkaline aqueous system is cooling water.

\* \* \* \* \*